(12) United States Patent
Ye

(10) Patent No.: US 10,696,629 B2
(45) Date of Patent: Jun. 30, 2020

(54) CRYSTALLINE FORM OF DEXTRAL OXIRACETAM, PREPARATION METHOD THEREFOR AND USE THEREOF

(71) Applicant: CHONGQING RUNZE PHARMACEUTICAL COMPANY LIMITED, Chongqing (CN)

(72) Inventor: Lei Ye, Chongqing (CN)

(73) Assignee: CHONGQING RUNZE PHARMACEUTICAL COMPANY LIMITED, Chongqing (CN)

( * ) Notice: Subject to any disclaimer, the term of this patent is extended or adjusted under 35 U.S.C. 154(b) by 0 days.

(21) Appl. No.: 16/344,337

(22) PCT Filed: Jul. 7, 2017

(86) PCT No.: PCT/CN2017/092219
§ 371 (c)(1),
(2) Date: Apr. 23, 2019

(87) PCT Pub. No.: WO2018/076782
PCT Pub. Date: May 3, 2018

(65) Prior Publication Data
US 2020/0071270 A1    Mar. 5, 2020

(30) Foreign Application Priority Data
Oct. 24, 2016   (CN) .......................... 2016 1 0985258

(51) Int. Cl.
*C07D 207/273* (2006.01)

(52) U.S. Cl.
CPC ...... *C07D 207/273* (2013.01); *C07B 2200/13* (2013.01)

(58) Field of Classification Search
CPC ................................................ C07D 207/273
See application file for complete search history.

(56) References Cited

U.S. PATENT DOCUMENTS

| 4,124,594 A | 11/1978 | Monguzzi |
| 4,173,569 A | 11/1979 | Banfi |
| 9,670,156 B2 * | 6/2017 | Ye .................... C07D 207/273 |
| 2019/0256464 A1 | 8/2019 | Ye |

FOREIGN PATENT DOCUMENTS

| CN | 102249977 A | 11/2011 |
| CN | 102442936 A | 5/2012 |
| CN | 102600130 A | 7/2012 |
| CN | 102603607 A | 7/2012 |
| CN | 103553998 A | 2/2014 |
| CN | 105330582 A | 2/2016 |
| CN | 105820101 A | 8/2016 |
| CN | 106166150 A | 11/2016 |
| KR | 20060010000 | 2/2006 |
| WO | 2018076782 | 5/2018 |
| WO | 2018076783 | 5/2018 |
| WO | 2018076784 | 5/2018 |
| WO | 2018130063 | 7/2018 |

OTHER PUBLICATIONS

International Application No. PCT/CN2017/118180; International Search Report (with translation) and Written Opinion of the International Searching Authority, dated Apr. 4, 2018; 12 pages.
Miyamoto, S., "Synthesis of 4-Hydroxy-2-Pyrrolidinone Derivatives", Neurosciences, 11:1-8, (1985).
Almeida, J. et al., "New Enantioselective Synthesis of 4-Hydroxy-2-Oxypyrrolidine-N-Acetamide (Oxiracetam) from Malic Acid", Tethrahedron: Asymmetry, 3(11):1431-40, (1992).
Chen, X. et al., "Synthesis of (R) 4-Hydroxy-Oxo-1-Pyrrolidineacetamide", Fine Chemical Intermediates, 41(5):21-3, (2011).
International Application No. PCT/CN2017/092219; International Search Report (with translation) and Written Opinion of the International Searching Authority, dated Oct. 11, 2017; 9 pages.
International Application No. PCT/CN2017/092220; International Search Report (with translation) and Written Opinion of the International Searching Authority, dated Oct. 11, 2017; 8 pages.
International Application No. PCT/CN2017/092221; International Search Report (with translation) and Written Opinion of the International Searching Authority, dated Sep. 27, 2017; 16 pages.

* cited by examiner

*Primary Examiner* — Joseph R Kosack
(74) *Attorney, Agent, or Firm* — Dennis A. Bennett; John Desper

(57) ABSTRACT

The present invention provides a crystalline form of dextral oxiracetam. The crystalline form has a diffraction peak when a diffraction angle, 2θ, is 17.12±0.2°, 18.88±0.2°, 19.24±0.2°, 21.18±0.2°, 24.88±0.2°. The crystalline form having oxiracetam can promote synthesis of phosphorylcholine and phosphoethanolamine, boosts cerebral metabolism, has a stimulating function on a specific central nervous pathway through a blood-brain barrier, improves the intelligence and memory, has an obvious effect on a memory dysfunction, and has special biologic activity in the field of sedation and the antiepileptic field. The method for preparing the crystalline form is simple and is suitable for industrial production.

11 Claims, 1 Drawing Sheet

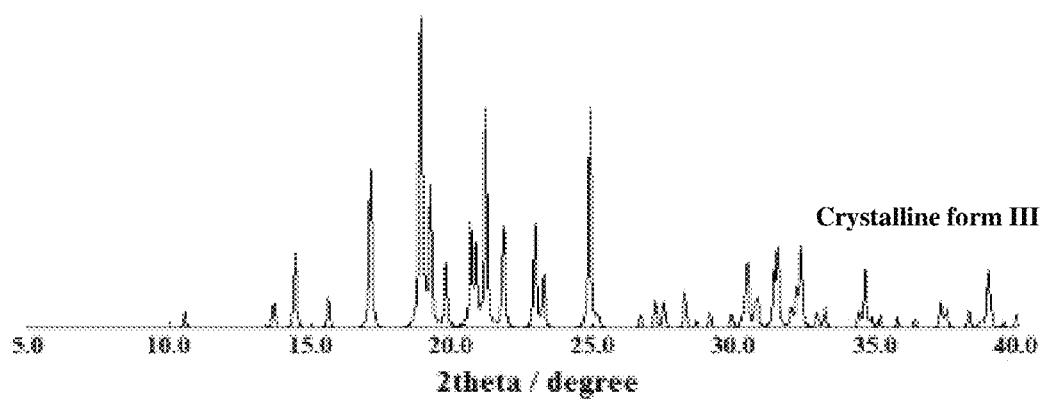

CRYSTALLINE FORM OF DEXTRAL OXIRACETAM, PREPARATION METHOD THEREFOR AND USE THEREOF

This application is a national stage entry of PCT/CN2017/092219, filed Jul. 7, 2017, which claims priority to Chinese patent application no. 201610985258.0, filed Oct. 24, 2016, the disclosures of which are hereby incorporated by reference as if written herein in their entireties.

TECHNICAL FIELD

The invention relates to dextral oxiracetam, particularly to a crystalline form of dextral oxiracetam, preparation method and use thereof.

BACKGROUND ART

Oxiracetam, its CAS No. is 62613-82-5, is a new generation of drug for improving cerebral metabolism that was first synthesized in 1974 by SmithKline Beecham Corporation, Italy and has been available on the market in 1987. Oxiracetam is capable of promoting synthesis of phosphorylcholine and phosphoethanolamine, promoting cerebral metabolism, stimulating specific central nervous pathways through blood-brain barrier, and improving intelligence and memory. Studies have shown that its levorotatory form has a better curative effect of promoting brain and intelligence development. In recent years, it has been reported that its dextrorotatory form (dextral oxiracetam) has special biological activity in the field of sedation and anti-epilepsy, and has low toxicity and a broad range of pharmaceutical safety. Therefore, dextral oxiracetam is expected to become an alternative to the existing highly toxic anti-epileptic drugs.

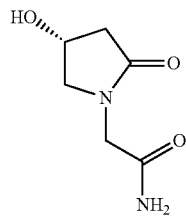

Dextral oxiracetam

In order to effectively develop dextral oxiracetam into pharmaceutical products, a solid form that is easy to manufacture and has acceptable chemical and physical stability is required to facilitate its processing and circulating storage. The crystalline solid form is generally superior to the amorphous form in terms of enhancing the purity and stability of the compound. At present, there are few studies on preparation methods and crystalline forms of dextral oxiracetam, and no crystalline form of dextral oxiracetam has been disclosed.

SUMMARY OF THE INVENTION

According to a first aspect of the invention, the invention provides a crystalline form of dextral oxiracetam, and the complete characteristics of the invention are described below, but for convenience, the provided crystalline form of dextral oxiracetam is referred to as "crystalline form III".

As set forth herein, all the parts are parts by weight, and all the percentages are mass percent, unless otherwise stated.

The object of the invention is achieved by:
a crystalline form III of dextral oxiracetam having diffraction peaks at diffraction angles 2θ of 17.12±0.2°, 18.88±0.2°, 19.24±0.2°, 21.18±0.2°, and 24.88±0.2°.

The crystalline form III of dextral oxiracetam described above has a relative peak intensity of 100% at the diffraction angle 2θ of 18.88±0.2°; a relative peak intensity of more than 80% and less than 100% at the diffraction angles 2θ of 21.18±0.2° and 24.88±0.2°; and a relative peak intensity of not less than 60% at the diffraction angles 2θ of 17.12±0.2° and 19.24±0.2°.

According to an embodiment of the invention, the crystalline form III of dextral oxiracetam described above has diffraction peaks at diffraction angles 2θ of 17.12±0.2°, 18.88±0.2°, 19.24±0.2°, 20.66±0.2°, 20.84±0.2°, 21.18±0.2°, 21.82±0.2°, 22.94±0.2°, 24.88±0.2°, and 31.52±0.2°.

According to an embodiment of the invention, the crystalline form III of dextral oxiracetam described above has diffraction peaks at diffraction angles 2θ of 14.44±0.2°, 17.12±0.2°, 18.88±0.2°, 19.24±0.2°, 19.78±0.2°, 20.66±0.2°, 20.84±0.2°, 21.18±0.2°, 21.82±0.2°, 22.94±0.2°, 23.24±0.2°, 24.88±0.2°, 30.46±0.2°, 31.40±0.2°, and 31.52±0.2°.

According to an embodiment of the invention, the crystalline form III of dextral oxiracetam described above has a powder diffraction pattern as shown in FIG. 1.

According to a second aspect of the invention, the invention provides a method of preparing the crystal form III of dextral oxiracetam, which has a simple process and is suitable for industrial production.

A method of preparing the crystal form III of dextral oxiracetam comprises the following steps: dissolving dextral oxiracetam in n-propanol to form a supersaturated solution, and then cooling the solution in a low temperature environment of from −12° C. to −21° C. to form crystals, separating the crystals by filtration, and drying to obtain the crystal form III of dextral oxiracetam.

According to an embodiment of the invention, the method of preparing the crystalline form III of dextral oxiracetam described above comprises the following steps: adding dextral oxiracetam into the n-propanol in a concentration of from 5 mg/mL to 55 mg/mL, stirring continuously, dissolving by heating at from 30° C. to 95° C., and filtering to form the supersaturated solution; and then sealing the supersaturated solution and cooling it in a low temperature environment of from −12° C. to −21° C. to form crystals, separating the crystals by filtration, and drying to obtain the crystal form III of dextral oxiracetam.

According to an embodiment of the invention, the method of preparing the crystalline form III of dextral oxiracetam described above comprises the following steps: adding dextral oxiracetam into the n-propanol in a concentration of from 10 mg/mL to 55 mg/mL, stirring continuously, dissolving by heating at from 35° C. to 90° C., and filtering to form the supersaturated solution; and then sealing the supersaturated solution and cooling it in a low temperature environment of from −12° C. to −21° C. to form crystals, separating the crystals by filtration, and drying to obtain the crystal form III of dextral oxiracetam.

According to an embodiment of the invention, the low temperature environment described above is from −17° C. to −20° C., and preferably from −17° C. to −19° C.

According to an embodiment of the invention, the method of preparing the crystalline form III of dextral oxiracetam described above comprises the following steps: adding dextral oxiracetam into the n-propanol in a concentration of from 5 mg/mL to 55 mg/mL, stirring continuously, dissolving by heating at from 35° C. to 65° C., and filtering to form the supersaturated solution; and then sealing the supersaturated solution and cooling it in a low temperature environment of from −17° C. to −19° C. to form crystals, separating the crystals by filtration, and drying at 30° C. to 80° C. and 0-20% relative humidity for 3-5 h, to obtain the crystalline form III of dextral oxiracetam.

The raw crystalline form of the dextral oxiracetam of the invention can be a commercially available product or can be self-made, and the remaining raw materials or reagents are all commercially available products. In the preparation of the crystalline form of the invention, the filtration is a conventional solid-liquid separation method well known in the art.

According to a third aspect of the invention, the invention provides use of the crystalline form III of dextral oxiracetam (in a therapeutically effective amount) for the preparation of anti-epileptic drugs. The invention provides use of the crystalline form III of dextral oxiracetam for the preparation of anti-epileptic drugs for preventing or treating acute seizures of epilepsy, in particular for the preparation anti-epileptic drugs for preventing or treating acute and severe seizures of epilepsy. The invention provides use of the crystalline form III of dextral oxiracetam for the preparation of anti-epileptic drugs for preventing or treating generalized seizures of epilepsy. The invention provides use of the crystalline form III of dextral oxiracetam for the preparation of anti-epileptic drugs for preventing or treating partial seizures of epilepsy. The invention provides use of the crystalline form III of dextral oxiracetam for the preparation of anti-epileptic drugs for preventing or treating status epilepticus. The crystalline form III of dextral oxiracetam of the invention exhibits special pharmacological activities in stabilization of abnormal cerebral discharge, sedation, anti-epilepsy, and the like; and it has solubility of more than or equal to 100 mg/mL in water, and a high bioavailability.

According to a fourth aspect of the invention, the invention provides a pharmaceutical composition comprising the crystalline form III of dextral oxiracetam described above, and pharmaceutically acceptable excipients. The composition is in any clinically acceptable pharmaceutical dosage form, including tablets, powders, granules, injections, capsules, dripping pills, sustained release formulations, and lyophilized powders for injection for administrations including (but not limited to) oral, rectal, transvaginal, nasal, inhalation, topical (including transdermal) or parenteral administration.

Advantageous Effects

The invention provides a crystalline form of dextral oxiracetam having diffraction peaks at diffraction angles 2θ of 17.12±0.2°, 18.88±0.2°, 19.24±0.2°, 21.18±0.2°, and 24.88±0.2°, and having a relative peak intensity of 100% at the diffraction angle 2θ of 18.88±0.2°; a relative peak intensity of more than 80% and less than 100% at the diffraction angles 2θ of 21.18±0.2° and 24.88±0.2°; and a relative peak intensity of not less than 60% at the diffraction angles 2θ of 17.12±0.2° and 19.24±0.2°. The crystalline form of dextral oxiracetam of the invention has oxiracetam that is capable of promoting synthesis of phosphorylcholine and phosphoethanolamine, promoting cerebral metabolism, stimulating specific central nervous pathways through blood-brain barrier, and has special biological activity in the field of sedation, anti-epilepsy, and the like. The crystalline form III of dextral oxiracetam of the invention has a high dissolution velocity in water, solubility of more than or equal to 100 mg/mL in water, and a high bioavailability. The crystalline form III of dextral oxiracetam of the invention does not show a phenomenon of crystal transformation at between 30° C. and 80° C., and has good stability in high temperatures. When the crystalline form III of dextral oxiracetam of the invention is used for storage or formulation processing, the requirements on processing and storage temperatures are reduced. The crystalline form III of dextral oxiracetam of the invention has good stability in high temperatures, fluidity and solubility in conventional solvents (such as water, methanol, DMSO, or the like), and the formulation process has a high adaptability. The crystalline form III of dextral oxiracetam of the invention is suitable for producing a variety of pharmaceutical compositions, which can be made into pharmaceutical preparations such as tablets, capsules, dripping pills, sustained release formulations, lyophilized powders for injection and so on. The preparation method of the invention adopts cheap and easily available raw material, and the prepared crystalline form III of dextral oxiracetam has a high purity. The preparation method requires mild conditions and simple operations, introduces a low level of impurities and has a good reproducibility; the production process is easy to control, has a high safety, and is suitable for industrial production.

BRIEF DESCRIPTION OF THE DRAWINGS

FIG. 1 is a powder diffraction pattern of the crystalline form III of dextral oxiracetam.

DEFINITIONS

When describing the compound, crystalline form, uses, compositions and methods of the invention, the following terms have the following meanings, unless otherwise stated.

The term "therapeutically effective amount" means an amount that is sufficient to effect treatment when the amount is administered to a patient in need of treatment. As used herein, the term "treating" means treating a disease, illness or medical condition of a patient, for example, mammal (particularly human), comprising:

(a) preventing the occurrence of the disease, illness or medical condition, namely preventive treatment of the patient;

(b) improving the disease, illness or medical condition, namely eliminating or regressing the disease, illness or medical condition of the patient, including counteracting effects of other therapeutic agents;

(c) inhibiting the disease, illness or medical condition, namely mitigating or prohibiting the development of the disease, illness or medical condition of the patient; or (d) alleviating the symptoms of the disease, illness or medical condition of the patient.

It is noted that the singular form "a(n)", "one" and "the", as in the specification and the appended claims, can include plural referents, unless otherwise clearly stated in the content.

DETAILED DESCRIPTION OF THE PREFERRED EMBODIMENTS

The invention is described in detail by the following examples. It should be pointed out that the following examples are intended to illustrate the invention, and are not to be construed as limiting the scope of the invention. Some non-essential modifications and adjustments to the invention can be made by those skilled in the art according to the aforementioned summary of the invention.

Preparation of Crystalline Form III of Dextral Oxiracetam

Example 1

30 mg of dextral oxiracetam (Chongqing Runze Pharmaceutical Co., Ltd.) was dissolved in 6 mL of n-propanol, heated at 40° C., and filtered to obtain a supersaturated solution. The solution was sealed and placed at −19° C. for 24 h for cooling crystallization, separated by filtration and dried at 70° C. and 10% relative humidity for approximately 5 h and obtained crystals.

Example 2

The crystallographic parameters of the crystals of dextral oxiracetam obtained in Example 1 were measured.

Powder Diffraction Measurement (XRPD):

Instrument and condition for measurement: the measurement was performed using the Bruker D2 PHASER powder diffractometer at room temperature. The measurement conditions were: Cu Kα(1.5418 Å) radiation as the light source, a voltage of 30 kV, a current of 10 mA, a test step length of 0.014°, a scanning rate of 0.1 s/step, and a scanning range of 5-40° (2θ). According to the measurement, the crystals of dextral oxiracetam prepared in Example 1 have diffraction peaks at diffraction angles 2θ of 14.44±0.2°, 17.12±0.2°, 18.88±0.2°, 19.24±0.2°, 19.78±0.2°, 20.66±0.2°, 20.84±0.2°, 21.18±0.2°, 21.82±0.2°, 22.94±0.2°, 23.24±0.2°, 24.88±0.2°, 30.46±0.2°, 31.40±0.2°, and 31.52±0.2°. For convenience, the crystals are referred to as "crystalline form III of dextral oxiracetam", the powder diffraction pattern thereof is shown in FIG. 1, and the analysis of diffraction data is presented as below.

TABLE 1

Powder diffraction peaks of crystalline form III
Crystalline form III of dextral oxiracetam

| Dihedral angle (°) | Intensity (I) |
|---|---|
| 10.54 | 23.9177 |
| 13.46 | 12.2463 |
| 13.7 | 28.7337 |
| 14.44 | 49.294 |
| 15.62 | 31.4916 |
| 17.12 | 71.307 |
| 18.88 | 100 |
| 19.24 | 68.1136 |

TABLE 1-continued

Powder diffraction peaks of crystalline form III
Crystalline form III of dextral oxiracetam

| Dihedral angle (°) | Intensity (I) |
|---|---|
| 19.78 | 46.0175 |
| 20.66 | 58.9972 |
| 20.84 | 52.8698 |
| 21.18 | 84.3275 |
| 21.82 | 57.3183 |
| 22.94 | 58.0554 |
| 23.24 | 41.7423 |
| 24.88 | 83.9511 |
| 25.16 | 22.47 |
| 26.68 | 21.0979 |
| 27.2 | 30.4529 |
| 27.5 | 28.9969 |
| 28.24 | 34.2199 |
| 28.64 | 15.1641 |
| 29.12 | 22.5944 |
| 29.88 | 21.8343 |
| 30.46 | 46.1025 |
| 30.72 | 29.3401 |
| 30.8 | 31.9314 |
| 31.4 | 43.8001 |
| 31.52 | 51.2459 |

As can be seen from Table 1 above, the crystalline form III of dextral oxiracetam of the invention has a relative peak intensity of 100% at the diffraction angle 2θ of 18.88±0.2°; a relative peak intensity of more than 80% and less than 100% at diffraction angles 2θ of the 21.18±0.2° and 24.88±0.2°; and a relative peak intensity of not less than 60% at the diffraction angles 2θ of 17.12±0.2° and 19.24±0.2°.

Single Crystal X-Ray Diffraction (SXRD) Measurement:

The used instrument was X-ray single crystal diffractometer (Gemini A Ultra, Agilent Inc., USA) with Cu Kα radiation at Emission λ=1.5418 Å, and the data were collected using ω/2θ scan. Data reduction and absorption correction were performed using CrysAlis PRO software. The space group was determined by extinction law of the system, and verified by the refinement results. Using SHELXS-97 program, the crystal structure was solved by the direct method, and the results were corrected by full-matrix least squares method, the coordinates of the hydrogen atoms on carbons were input according to the theoretical calculation, and the coordinates of the hydrogen atoms on the other atoms were input according to calculation by electron density map. The crystallographic parameters of the crystalline form III of dextral oxiracetam of the invention are shown in Table 2 below.

TABLE 2

Crystal data and structure refinement for exp_9421.

| | |
|---|---|
| Identification code | exp_9421 |
| Empirical formula | C12 H20 N4 O6 |
| Formula weight | 316.32 |
| Measurement temperature | 293(2) K |
| Wavelength | 1.54184 A |
| Crystal system, space group | Tetragonal, P 4$_3$ |
| Unit cell dimensions | a = 6.58320(6) A alpha = 90 deg. |
| | b = 6.58320(6) A beta = 90 deg. |
| | c = 33.5187(4) A gamma = 90 deg. |
| Unit cell volume | 1452.65(3) A^3 |
| Z, Calculated density | 4, 1.446 Mg/m^3 |
| Absorption coefficient | 0.993 mm^−1 |
| Structure factor F(000) | 672 |
| Crystal size | 0.10 × 0.05 × 0.03 mm |
| Theta range for date collection | 5.28 to 63.65 deg. |

TABLE 2-continued

Crystal data and structure refinement for exp_9421.

| | |
|---|---|
| Crystal surface index range (Limiting indices) | $-7 <= h <= 7, -7 <= k <= 7, -38 <= l <= 38,$ |
| Total number of diffraction points/ Number of independent diffraction points (Reflections collected/unique) | 12456/2394 [R(int) = 0.0273] |
| Completeness to theta = 63.65 | 100.0% |
| Absorption correction | Semi-empirical from equivalents |
| Max. and min. transmission | 0.9708 and 0.9072 |
| Refinement method | Full-matrix least-squares on F^2 |
| Independent diffraction point data/restraints/refinement parameters (data/restraints/parameters) | 2394/1/201 |
| Goodness of fit factor GOOF value (Goodness-of-fit onF^2) | 1.073 |
| R indices [I > 2σ(I)]* (Final R indices [I > 2sigma(I)]) | R1 = 0.0233, wR2 = 0.0576 |
| R indices (all data) | R1 = 0.0238, wR2 = 0.0580 |
| Absolute structure parameter | 0.12(14) |
| Maximum residual electron peak/hole (Largest diff. peak and hole) | 0.100 and −0.194 e.A^−3 |

*$R_1 = \Sigma ||F_o| - |F_c||/\Sigma|F_o|$, $wR_2 = [\Sigma w(F_o^2 - F_c^2)^2/\Sigma w(F_o^2)^2]^{1/2}$, $w = [\sigma^2(F_o)^2 + (0.1(\max(0, F_o^2) + 2F_c^2)/3^2]^{-1}$ As can be seen from the Table 2 above, the crystalline form III of dextral oxiracetam of the invention is a tetragonal system, Tetragonal, P 4$_3$, where, a=6.58320(6)A alpha=90 deg., b=6.58320(6)A beta=90 deg., and c=33.5187(4)A gamma=90 deg.

Referring to Example 1, the crystalline form III of dextral oxiracetam was prepared according to Examples 3-6.

Example 3

30 mg of dextral oxiracetam was dissolved in 2 mL of n-propanol, heated at 50° C., and filtered to obtain a supersaturated solution. The solution was sealed and placed at −17° C. for 15 h for cooling crystallization, separated by filtration and dried at 65° C. and 10% relative humidity for approximately 4 h and obtained colorless, sandy crystals. The crystals were identified as a crystal form III of dextral oxiracetam by using the method in Example 2.

Example 4

6 mg of dextral oxiracetam was dissolved in 1 mL of n-propanol, heated at 40° C., and filtered to obtain a supersaturated solution. The solution was sealed and placed at −15° C. for 20 h for cooling crystallization, separated by filtration and dried at 30° C. and 10% relative humidity for approximately 3 h, and obtained colorless, sandy crystals. The crystals were identified as a crystal form III of dextral oxiracetam by using the method in Example 2.

Example 5

60 mg of dextral oxiracetam was dissolved in 5 mL of n-propanol, heated at 50° C., and filtered to obtain a supersaturated solution. The solution was sealed and placed at −19° C. for 36 h for cooling crystallization, separated by filtration and dried at 80° C. and 20% relative humidity for approximately 4 h and obtained colorless, sandy crystals. The crystals were identified as a crystal form III of dextral oxiracetam by using the method in Example 2.

Example 6

100 mg of dextral oxiracetam was dissolved in 4 mL of n-propanol, heated at 50° C., and filtered to obtain a supersaturated solution. The solution was sealed and placed at −18° C. for 36 h for cooling crystallization, separated by filtration and dried at 45° C. and 12% relative humidity for approximately 6 h and obtained colorless, sandy crystals. The crystals were identified as a crystal form III of dextral oxiracetam by using the method in Example 2.

Performance Measurement Experiment of Crystalline Form III of Dextral Oxiracetam Example 7

The crystalline form III of dextral oxiracetam of the invention was placed on a single crystal silicon sample stage, heated from 30° C. to 80° C., and subjected to powder X-ray diffraction measurement at 35° C., 45° C., 55° C., 65° C. and 75° C., respectively. The test results show that the crystalline form III of dextral oxiracetam of the invention does not exhibit crystal transformation phenomenon between 30° C. and 80° C. It can be seen that the crystalline form III of dextral oxiracetam of the invention has good stability at high temperatures. From the variable-temperature powder test on the crystalline form III of dextral oxiracetam, it is found that the crystalline form III of dextral oxiracetam did not exhibit crystal transformation phenomenon prior to being melt. It can be confirmed that the crystalline form III of dextral oxiracetam is temperature stable. When the crystalline form III of dextral oxiracetam of the invention is used for storage or formulation processing, the requirements on processing and storage temperatures are reduced.

Preparation of Compositions Comprising Crystalline Form III of Dextral Oxiracetam Example 8

1000 capsules comprising crystalline form III of dextral oxiracetam were taken as examples, which were prepared by using 180 mg/capsule of the crystalline form III of dextral oxiracetam prepared by the method in Example 1, 90.8 mg/capsule of lactose, 82 mg/capsule of sodium carboxymethyl starch, 7.2 mg/capsule of talcum powder and an appropriate amount of 10% polyvinylpyrrolidone. The specific preparation method was given as follows: the raw materials and excipients were firstly passed through an 80-mesh sieve; the above-mentioned amounts of crystalline form III of dextral oxiracetam, lactose and sodium carboxymethyl starch were weighed and mixed uniformly, and 10% PVP ethanol solution was added to produce a soft material, pelletized, dried and granulated; the above-mentioned amount of talcum powder was added to the granules, mixed uniformly and filled into the capsules.

Example 9

1000 tablets comprising crystalline form III of dextral oxiracetam were taken as examples, which were prepared by using 200 mg/tablet of the crystalline form III of dextral oxiracetam prepared by the method in Example 1, 44 mg/tablet of starch, 50 mg/tablet of microcrystalline cellulose, 6 mg/table of talcum powder and an appropriate amount of 2% hydroxypropyl methylcellulose (K4M). The specific preparation method was given as follows: the raw materials and excipients were firstly passed through an 80-mesh sieve; the above-mentioned amounts of crystalline form III of dextral oxiracetam, starch and microcrystalline cellulose were weighed and mixed uniformly, and an appropriate amount of 2% HPMC aqueous solution was added to produce a soft material, pelletized, dried and granulated; the prescription amount of talcum powder was added to the granules, mixed uniformly and pressed into the tablets.

Example 10

60 g of the crystalline form III of dextral oxiracetam prepared by the method in Example 1 and 140 g of glucose were dissolved in 500 ml of water for injection in a mixing equipment under controlling the temperature between 50° C. and 58° C., and stirred until completely dissolved. The solution was cooled to 25° C. The activated carbon was added into the above prepared solution for decolorization, and then the activated carbon was removed by filtration. Phosphate buffer was added to adjust pH of the solution to 4.0, followed by adding water for injection to 5000 ml, filling and sealing, and sterilizing at 105° C. for 30 min, and obtained an injection.

The invention claimed is:

1. A crystalline form III of dextral oxiracetam having diffraction peaks at diffraction angles 2θ of 17.12±0.2°, 18.88±0.2°, 19.24±0.2°, 21.18±0.2°, and 24.88±0.2°.

2. The crystalline form III of dextral oxiracetam according to claim 1, characterized in that the crystalline form III of dextral oxiracetam has a relative peak intensity of 100% at the diffraction angle 2θ of 18.88±0.2°; a relative peak intensity of more than 80% and less than 100% at diffraction angles 2θ of 21.18±0.2° and 24.88±0.2°; and a relative peak intensity of not less than 60% at the diffraction angles 2θ of 17.12±0.2° and 19.24±0.2°.

3. The crystalline form III of dextral oxiracetam according to claim 1, characterized in that the crystalline form III of dextral oxiracetam has diffraction peaks at diffraction angles 2θ of 17.12±0.2°, 18.88±0.2°, 19.24±0.2°, 20.66±0.2°, 20.84±0.2°, 21.18±0.2°, 21.82±0.2°, 22.94±0.2°, 24.88±0.2°, and 31.52±0.2°.

4. The crystalline form III of dextral oxiracetam according to claim 1, characterized in that the crystalline form III of dextral oxiracetam has diffraction peaks at diffraction angles 2θ of 14.44±0.2°, 17.12±0.2°, 18.88±0.2°, 19.24±0.2°, 19.78±0.2°, 20.66±0.2°, 20.84±0.2°, 21.18±0.2°, 21.82±0.2°, 22.94±0.2°, 23.24±0.2°, 24.88±0.2°, 30.46±0.2°, 31.40±0.2°, and 31.52±0.2°.

5. The crystalline form III of dextral oxiracetam according to claim 1, characterized in that the crystalline form has a powder diffraction pattern as shown in FIG. 1.

6. A method of preparing the crystalline form III of dextral oxiracetam according to claim 1, applying the following steps: dissolving dextral oxiracetam in n-propanol to form a supersaturated solution, and then cooling the solution in a low temperature environment of from −12° C. to −21° C. to form crystals, separating the crystals by filtration, and drying to obtain the crystal form III of dextral oxiracetam.

7. The method of preparing the crystalline form III of dextral oxiracetam according to claim 6, characterized in that the method applies the following steps: adding dextral oxiracetam into the n-propanol in a concentration of from 10 mg/mL to 55 mg/mL, stirring continuously, dissolving by heating at from 35° C. to 90° C., and filtering to form the supersaturated solution; then sealing the supersaturated solution and cooling it in a low temperature environment of from −12° C. to −21° C. to form crystals, separating the crystals by filtration, and drying to obtain the crystal form III of dextral oxiracetam.

8. The method of preparing the crystalline form III of dextral oxiracetam according to claim 6, characterized in that the low temperature environment is from −17° C. to −19° C.

9. A method for treating or preventing epilepsy in a patient in need thereof comprising: administering the crystalline form III of dextral oxiracetam according to claim 1.

10. The method of claim 9, wherein the crystalline form III of dextral oxiracetam is administered in the form of a pharmaceutical composition comprising the crystalline form III of dextral oxiracetam and pharmaceutically acceptable excipients.

11. The method according to claim 10, characterized in that the composition is tablets, powders, granules, injections, capsules, dripping pills, sustained release formulations, or lyophilized powders for injection.

* * * * *